United States Patent [19]
Errico et al.

[11] Patent Number: 5,554,157
[45] Date of Patent: Sep. 10, 1996

[54] ROD SECURING POLYAXIAL LOCKING SCREW AND COUPLING ELEMENT ASSEMBLY

[75] Inventors: Joseph P. Errico, Hempstead, N.Y.; Thomas J. Errico, Summit; James D. Ralph, Oakland, both of N.J.

[73] Assignee: Fastenetix, L.L.C., Summit, N.J.

[21] Appl. No.: 502,048

[22] Filed: Jul. 14, 1995

Related U.S. Application Data

[63] Continuation-in-part of Ser. No. 502,285, Jul. 13, 1995.

[51] Int. Cl.⁶ .................................................. A61B 17/70
[52] U.S. Cl. ............................... 606/61; 606/73; 606/60
[58] Field of Search ................................ 606/61, 69, 70, 606/71, 72, 73, 66, 65, 60, 59, 54, 104; 623/17, 16

[56] References Cited

U.S. PATENT DOCUMENTS

| | | | |
|---|---|---|---|
| 4,805,602 | 2/1989 | Puno et al. | 128/69 |
| 4,946,458 | 8/1990 | Harms et al. | 606/61 |
| 4,987,892 | 1/1991 | Krag et al. | 606/61 |
| 5,057,111 | 10/1991 | Park | 606/69 |
| 5,129,388 | 7/1992 | Vignaud et al. | 606/61 |
| 5,176,680 | 1/1993 | Vignaud et al. | 606/61 |
| 5,190,543 | 3/1993 | Schläpfer | 606/61 |
| 5,207,678 | 5/1993 | Harms et al. | 606/61 |
| 5,217,497 | 6/1993 | Mehdian | 623/17 |
| 5,261,909 | 11/1993 | Sutterlin et al. | 606/61 |
| 5,261,912 | 11/1993 | Frigg | 606/61 |
| 5,261,913 | 11/1993 | Marnay | 606/61 |
| 5,306,275 | 4/1994 | Bryan | 606/61 |
| 5,360,431 | 11/1994 | Puno et al. | 606/72 |
| 5,443,467 | 8/1995 | Biedermann et al. | 606/65 |
| 5,480,401 | 1/1996 | Navas | 606/61 |

*Primary Examiner*—Guy Tucker
*Attorney, Agent, or Firm*—Joseph P. Errico

[57] ABSTRACT

A polyaxial orthopedic device for use with rod implant apparatus includes a screw having a curvate head and a generally hollow coupling element. The coupling element includes an interior axial passage having an interior surface which is inwardly curvate at the lower portion thereof such that it comprises a socket for polyaxially retaining the curvate head of the screw. The coupling element further includes a pair of vertically oriented opposing channels extending down from the top of the coupling element, which define therebetween a rod receiving locus. The channel further divides the walls of the upper portion into a pair of upwardly extending members, each including an exterior threading disposed on the upper most portion for receiving a locking nut. During implantation of the assembly, the locking nut seats against the top of the rod, which in turn seats on the top of the screw head. Downward translation of the nut causes the rod to be locked between the nut and the screw and the screw to be locked in the socket. A preferred variation of the invention includes tapered upwardly extending members which deflect inward to additionally lock the rod from the sides.

2 Claims, 6 Drawing Sheets

5,554,157

ROD SECURING POLYAXIAL LOCKING SCREW AND COUPLING ELEMENT ASSEMBLY

BACKGROUND OF THE INVENTION

CROSS-REFERENCE TO PRIOR APPLICATION

This application is a continuation-in-part of prior application U.S. Ser. No. 08/502,285, entitled "An Advanced Polyaxial Locking Screw and Coupling Element For Use With Rod Fixation Apparatus", filed Jul. 13, 1995, still pending.

1. Field of the Invention

This invention relates generally to a polyaxial screw and coupling apparatus for use with orthopedic fixation systems. More particularly, the present invention relates to a screw for insertion into spinal bone, and a coupling element polyaxially mounted thereto for coupling the screw to an orthopedic implantation structure, such as a rod, therein enhancing the efficacy of the implant assembly by providing freedom of angulation among the rod, screw and coupling element.

2. Description of the Prior Art

The spinal column is highly complex system of bones and connective tissues which houses and protects critical elements of the nervous system and the arterial and veinous bodies in close proximity thereto. In spite of these complexities, the spine is a highly flexible structure, capable of a high degree of curvature and twist through a wide range of motion.

Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column. These assemblies may be classified as anterior, posterior, or lateral implants. As the classification suggests, lateral and anterior assemblies are coupled to the anterior portion of the spine, which is the sequence of vertebral bodies. Posterior implants are attached to the back of the spinal column, generally hooking under the lamina and entering into the central canal, attaching to the transverse process, or coupling through the pedicle bone. The present invention relates to spinal fixation devices for immobilizing and altering the alignment of the spine over a large number, for example more than three or four, vertebra by means of affixing at least one elongate rod to the sequence of selected bones.

Such "rod assemblies" generally comprise a plurality of screws which are implanted through the posterior lateral surfaces of the laminae, through the pedicles, and into their respective vertebral bodies. The screws are provided with coupling elements, for receiving an elongate rod therethrough. The rod extends along the axis of the spine, coupling to the plurality of screws via their coupling elements. The aligning influence of the rod forces the spine to which it is affixed, to conform to a more proper shape.

It has been identified, however, that a considerable difficulty is associated with inserting screws along a misaligned curvature and simultaneously exactly positioning the coupling elements such that the receiving loci thereof are aligned so that the rod can be passed therethrough without distorting the screws. Attempts at achieving proper alignment with fixed screws is understood to require considerably longer operating time, which is known to increase the incidence of complications associated with surgery. Often such alignments, with such fixed axes devices could not be achieved, and the entire instrumentationing effort would end unsuccessfully.

In addition, for many patients specific pathology it is desirable that the rod extend down into and beyond the lumbar portion of the spine, and for the end of the rod to be coupled to the sacral bone. Providing such an end to the assembly in the sacral bone has been understandably suggested inasmuch as it provides superior support to the full extent of the assembly. The most suitable position for the insertion of the screws into the sacral body may not, however, conform to the direction extent of the rod as it is affixed to the entirety of the assembly. Misalignment of the rod with respect to the screw and the coupling element is often a source of considerable disadvantage for the surgeon, often requiring considerable efforts to be expended bending and aligning the rod with the receiving locus of the coupling element. These additional efforts are a considerable difficulty associated with the proper and expeditious affixation, and over the long term, the offset of the rod can have a deleterious effect on the overall performance of the entire implantation assembly.

The art contains a variety of attempts at providing instrumentation which permit a freedom with respect to angulation of the screw and the coupling element. These teachings, however, have generally been complex, and inadequately reliable with respect to durability. The considerable drawbacks associated with the prior art systems include complexity, difficulty properly positioned the rod and coupling elements, and the tedious manipulation of the many parts associated with the complex devices.

It is, therefore, the principal object of the present invention to provide a pedicle screw and coupling element assembly which provides a polyaxial freedom of implantation angulation with respect to rod reception.

In addition, it is an object of the present invention to provide such an assembly which comprises a reduced number of elements, and which correspondingly provides for expeditious implantation.

Accordingly it is also an object of the present invention to provide an assembly which is reliable, durable, and provides long term fixation support.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a polyaxial locking screw and coupling element for use with rod stabilization and immobilization systems in the spine. More particularly, the polyaxial screw and coupling element assembly of the present invention comprise a bone screw having a head which is curvate in shape, for example semi-spherical, and a coupling element mounted thereon so as to be free to rotate prior to the secure fixation of the rod thereto, and which may be securely locked in a given angulation once the rod is received by the coupling element. The coupling element has a hollow cylindrical main body portion which includes a vertical channel for receiving the rod therein, and an inner passage which curves inward at the bottom for retaining therein the head of the polyaxial screw. The coupling element further comprises an exterior threading thereon for receiving a top locking nut.

The coupling element may be conceptually divided into a lower socket portion, a rod receiving portion, and a top nut receiving portion. The hollow cylindrical body comprises an axial passage which is ideally suited for receiving the screw therethrough. The passage curves inward at the bottom, thereby forming the lower socket portion inasmuch as the inner surface of the axial interior passage curves inward to conformally receive, securely and fittedly, the curvate head of the screw.

The rod receiving portion of the coupling element comprises a channel wherein the rod of the implant apparatus is mounted. More particularly, the walls of the hollow cylindrical body include opposing vertically oriented channels, having curvate bottom surfaces thereof, and which extend downward from the top of the element to a position above the lower portion. The channels divide the walls of the intermediate and upper portions of the cylindrical body into two upwardly extending members, between which the rod receiving channel is disposed. The lower socket portion of the element and the bottom portion of the rod receiving channel are proximally disposed such that the rod which is inserted into the channel rests upon the curvate head of the screw when both are properly positioned for assembly.

The upper portion of the upwardly extending members of the element comprise an external surface threading onto which a locking nut may be disposed to provide a downward force onto the rod. The downward force of the sleeve is translated, through a downward force of the rod, onto the head of the screw. The head of the screw is thereby crush locked against the inwardly curves walls of the interior passage, within the socket, such that the coupling element and the screw may be maintain in a specific angulation.

In a preferred variation, the threading is tapered slightly outward at the bottom so that when the locking nut which is driven downward thereon it may also provide an inward force against the upwardly extending members. The inward force on the upwardly extending members causes them to deflect inward, therein crush locking the rod within the rod receiving channel from the sides as well.

The first step in the process of implanting this invention is to insert the screw down the interior passage of the coupling element until the curvate head of the screw is nested properly within the lower socket portion. In this position the bottom surface of the curvate head and the inwardly curved walls of the inner passage are conformally matched so as to permit a rotational freedom of angulation therebetween.

Once the screw has been so positioned, the angle of bone insertion, at which the screw will have the greatest holding strength relative to the loading which the rod system will be applying thereto, is determined. Once this angle has been found, the screw and the coupling element are aligned with respect to one another so that a screw-driving tool may be inserted down the interior passage, into the recess in the head of the screw, whereby the screw may be rotationally inserted into the bone.

Subsequent to the insertion of the screw, the screw-driving device is removed from the assembly, and the coupling element is rotated to change angular alignment relative to the screw. The rod of the implantation apparatus is then provided into the opposing rod receiving channels, and is positioned so that it rests slightly above the curvate bottom thereof. The bottom of the rod, in fact, rests against the top of the curvate head of the screw, which, prior to final assembly of the device, extends above the bottom of the opposing channels.

Once the rod has been properly positioned, the top locking nut is then introduced onto the threaded top of the coupling element until the bottom of the nut seats against the top of the rod. The final act of tightening the top locking nut down onto the rod causes it to descend slightly, fully nesting at the curvate bottom of the rod receiving channels, and causing the head of the screw to crush lock to the curvate inner surface of the coupling element. As stated above, in a preferred embodiment in which the top threading includes a taper, tightening the nut causes the upwardly extending members to deflect inward, thereby additionally crush locking the rod from the sides.

In addition, it shall be understood that the curvate shape of the head of the screw may be chosen from the various specific shapes which are compatible with the general polyaxial concept of the present invention. For the purposes of providing specific variations of the embodiments described above, and set forth more fully hereinbelow with respect to the drawings, the shape of the screw head is semi-spherical. However, it is understood that one skilled in the art could easily alter the shape of the head, for example to have a flat top, or one having a crescent shape with a concave top and a convex bottom. The choice of using such alternate profiles versus a fully semi-spherical profile may be associated with the height of the overall screw and coupling element, inasmuch as the semispherical (or ball) head of the screw permits a higher seating of the coupling element versus the flattened or crescent shaped heads.

Multiple screw and coupling element assemblies are generally necessary to complete the full array of anchoring sites for the rod immobilization system, however, the screw and coupling element assembly of the present invention is designed to be compatible with alternative rod systems so that, where necessary, the present invention may be employed to rectify the failures of other systems the implantation of which may have already begun.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 1:
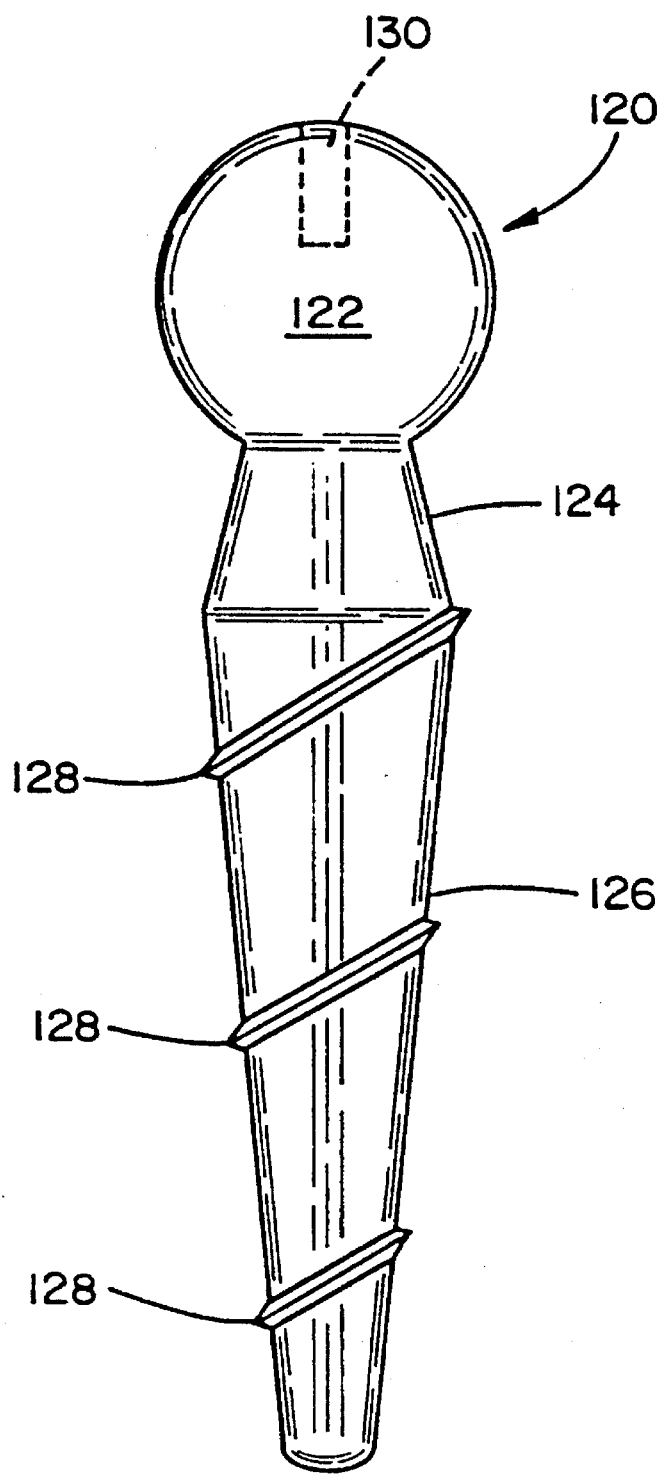
FIG. 1 is a side view of a screw having a curvate head which is an aspect of the present invention.

Referring now to FIG. 1, a side view of the screw portion of the present invention, comprising a curvate head, is shown. The screw 120 comprises a head portion 122, a neck 124, and a shaft 126. In FIG. 1, the shaft 126 is shown as having a tapered shape with a high pitch thread 128. It shall be understood that a variety of shaft designs are interchangeable with the present design. The specific choice of shaft features, such as thread pitch, shaft diameter to thread diameter ratio, and overall shaft shape, should be made be the physician with respect to the conditions of the individual patient's bone, however, this invention is compatible with a wide variety of shaft designs.

The head portion 122 of the screw 120 comprises a semi-spherical shape, which has a recess 130 in it. It is understood that the semi-spherical shape is a section of a sphere, in the embodiment shown the section is greater in extent than a hemisphere, and it correspondingly exhibits an external contour which is equidistant from a center point of the head. In a preferred embodiment, the major cross-section of the semi-spherical head 122 (as shown in the two dimensional illustration of FIG. 5) includes at least 270 degrees of a circle.

The recess 130 defines a receiving locus for the application of a torque for driving the screw 120 into the bone. The specific shape of the recess 122 may be chosen to cooperate with any suitable screw-driving tool. For example, the recess 130 may comprise a slot for a flat-headed screwdriver, a crossed recess for a phillips head screwdriver, or most preferably, a hexagonally shaped hole for receiving an allen wrench. It is further preferable that the recess 130 be co-axial with the general elongate axis of the screw 120, and most particularly with respect to the shaft 126. Having the axes of the recess 130 and the shaft 126 co-linear facilitates step of inserting the screw 120 into the bone.

The semi-spherical head portion 122 is connected to the shaft 126 at a neck portion 124. While it is preferable that the diameter of the shaft 126 be less than the diameter of the semi-spherical head 122, it is also preferable that the neck 124 of the screw 120 be narrower than the widest portion of the shaft 126. This preferable dimension permits the screw to be locked at a variety of angles while still being securely joined to the coupling element (embodiments of which are shown in FIGS. 2, 3 and 7).

Figure 2:
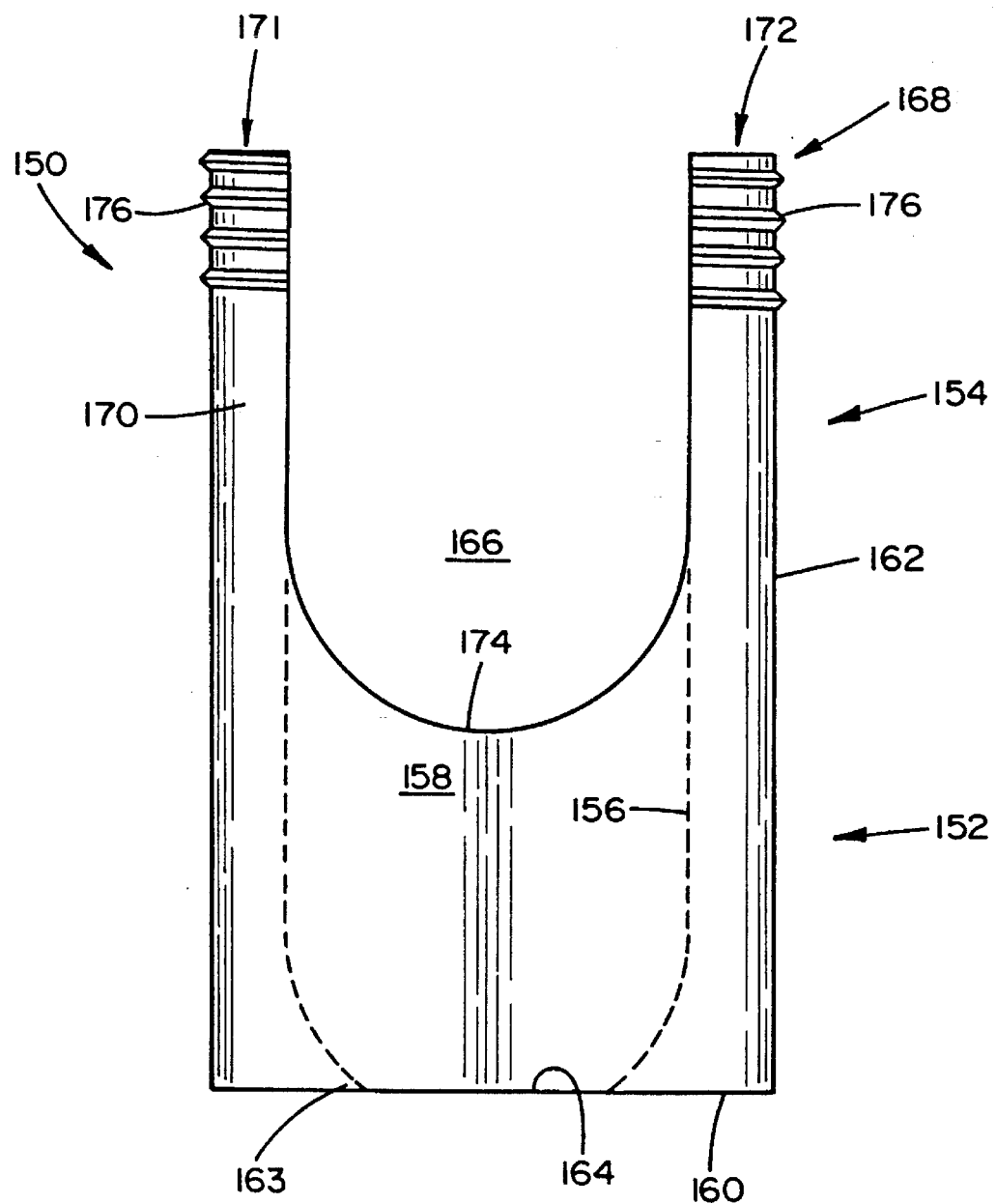
FIG. 2 is a side view of the coupling element of present invention, wherein critical interior features of the element are shown in phantom.
Figure 3:
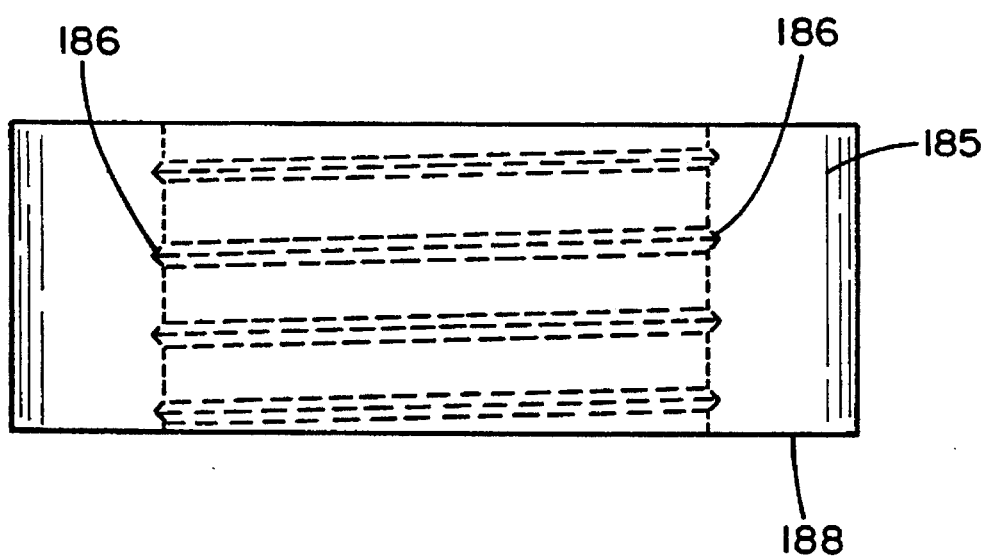
FIG. 3 is a side cross-sectional view of the top locking nut of the present invention.

Referring now to FIG. 2, a first embodiment of the coupling element 150 of the present invention is shown in a side view, wherein critical features of the interior of the element are shown in phantom. The coupling element 150 comprises a generally cylindrical tubular body which may be conceptually separated into a lower portion 152, and an upper portion 154, each of which shall be described more fully hereinbelow.

Figure 4:
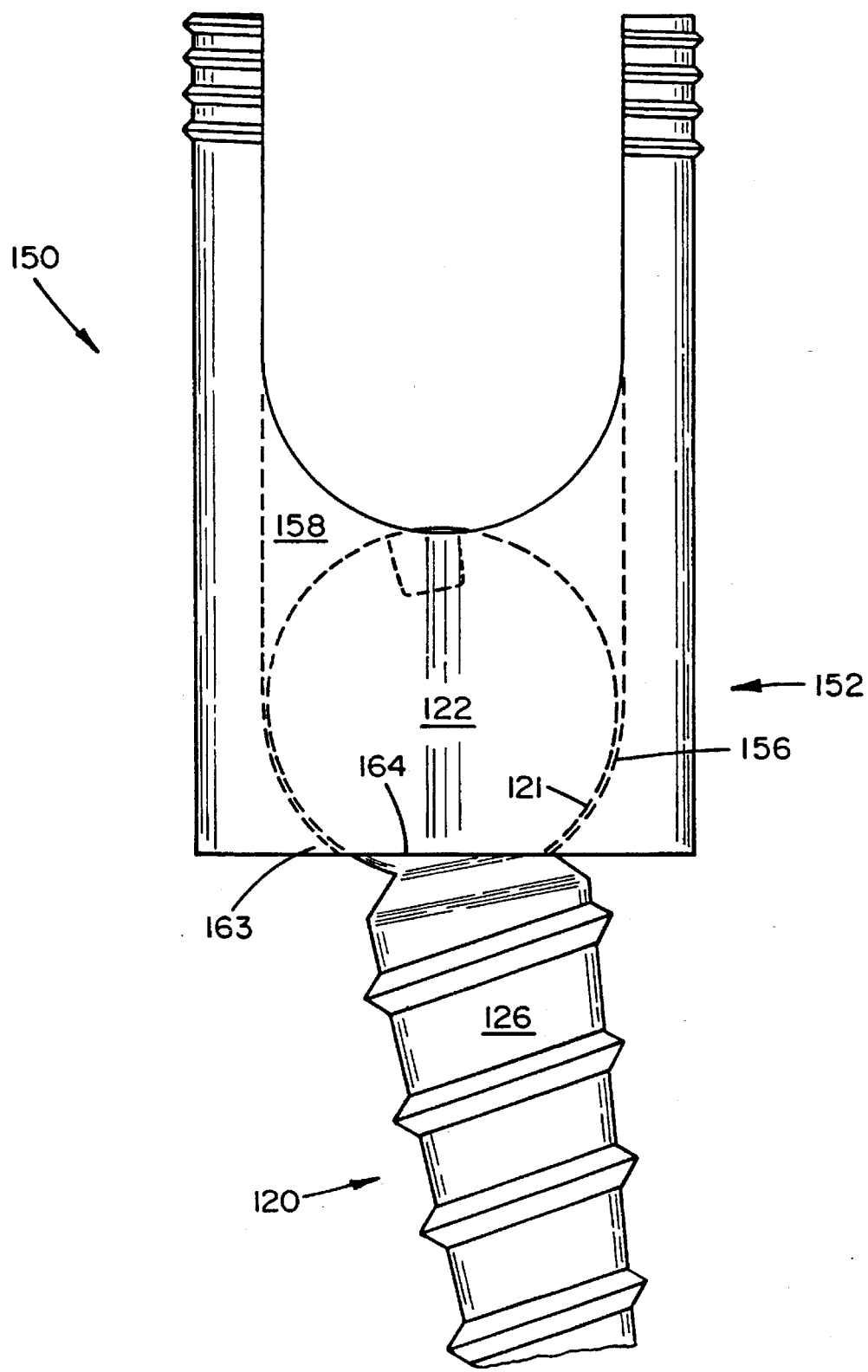
FIG. 4 is a side view of the coupling element of the present invention, as shown in FIG. 2, wherein the curvate head of a polyaxial screw is positioned within the lower socket portion thereof.

First, with respect to the lower portion 152, the interior surface 156 of the inner passage 158 is inwardly curvate, such that the passage 158 is narrower at the bottom 160 of the lower portion 152 than at the top 162 thereof. This inwardly curvate surface 156 defines a socket, into which the head 122 of the screw 120 may nest. The bottom 160 of the element includes an opening 164, defined by annular lip 163, which forms the narrowed mouth of an interior passage 158. Once assembled (see FIGS. 4, 5, and 6) the shaft 126 of the screw 120 extends through the opening 164. The diameter of the opening 164, therefore, must be greater than the diameter of the shaft 126 of the screw 120, but less than the major diameter of the head 122.

The upper portion 154 of the coupling element 150 includes a pair of opposing, vertically oriented, channels 166 having rounded bottom surfaces 174 thereof. The channels 166, together, form a rod receiving locus descending downward from the top 168 of the coupling element 150. The channels 166, defining the rod receiving locus, in turn, divide the wall 170 into upwardly extending members 171,172. As shown in the embodiment illustrated in FIG. 2, the vertical distance from the top 168 of the channel 166 to the curvate bottom 174 thereof, is larger than the diameter of the rod which is to be provided therein. This distance is necessarily larger than the diameter of the rod (see FIGS. 5 and 6) so that the rod may be fully nested in the channels 166. In fact the depth of the bottom curvate surface 174 of the channels 166 is such that the top of the head 122 of the screw 120, when fully nested in the lower socket portion 152, is thereabove.

The top 168 of the upper portion 154, which comprises upwardly extending members 171,172, have disposed thereon a threading 176. The upper portion 154, and the threading 176 thereon, is ideally suited for receiving a top locking nut (see FIG. 3).

Referring now to FIG. 3, a top locking nut 185 is shown in a side cross-section view. The nut 185 comprises an inner threading 186 which is intended to mate with the threading 176 on the upwardly extending members 171,172 of the upper portion 154 of the coupling element 150. The bottom surface 188 of the nut 185 is intended to seat against the top surface of the rod 190, but is permitted to rotate relative thereto, therein providing a means for driving the rod downward (as more fully described hereinbelow with respect to the full assembly of the device, and with respect to FIGS. 5 and 6).

Referring now to FIG. 3, the coupling element 150 is shown with the screw 120 inserted therethrough, and the head 122 of the screw 120 nested in the lower socket portion 152 thereof. The shaft portion 126 of the screw 120 is inserted downward, through the interior passage 158 of the coupling element 150, and out through the opening 164. In this position, the curvate undersurface 121 of the head 122 rests against the inwardly curved surface 156 of the lower socket portion 152, and is prevented from translating further downward by the annular lip 163 which defines the opening 164.

Figure 5:
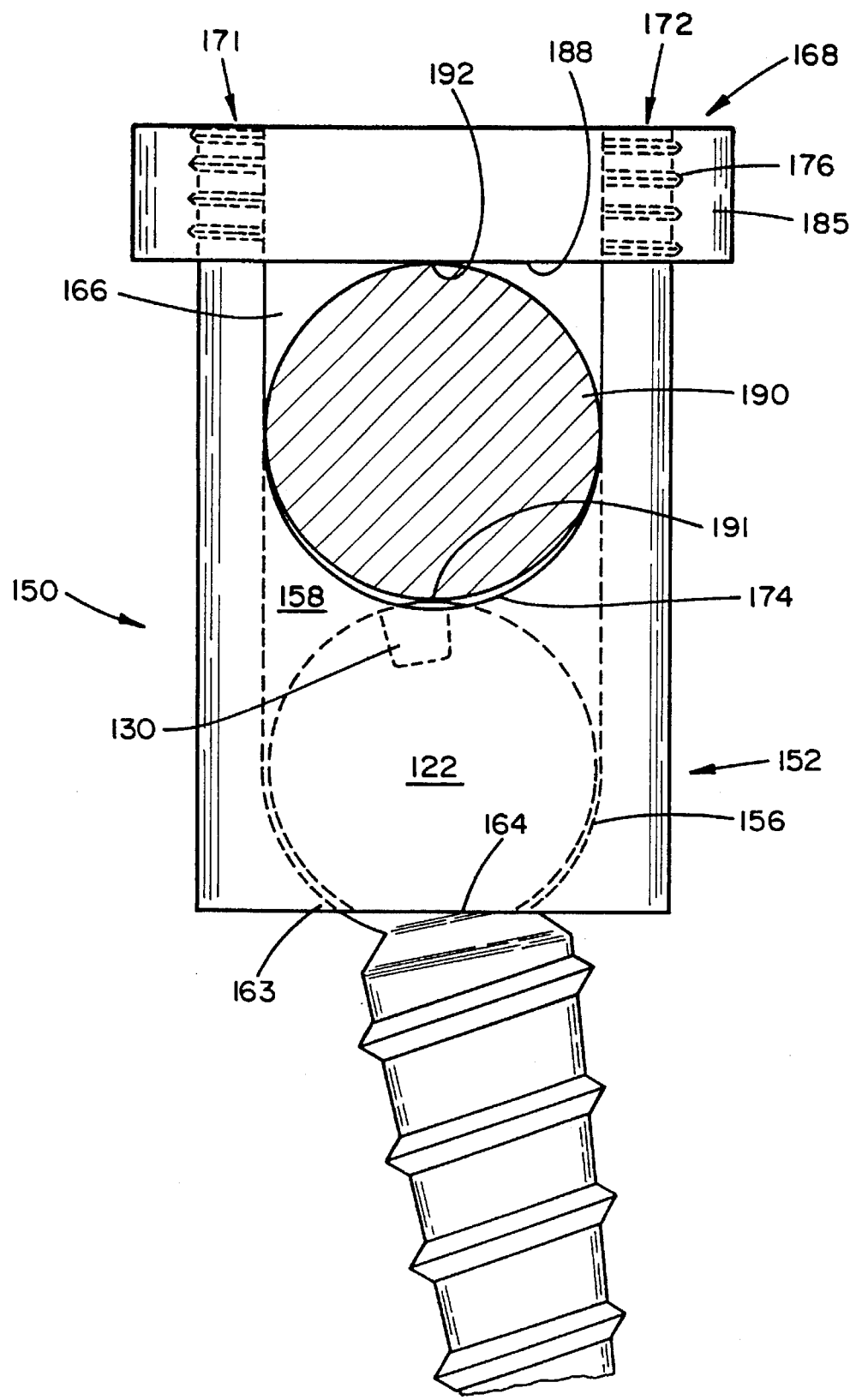
FIG. 5 is a side cross-sectional view of the present invention in its fully assembled disposition having a rod securely locked therein.

Referring now to FIG. 5, which shows a side view of the fully locked coupling element, rod, and screw system, the preferred method of implantation and assembly is described hereinbelow. First, a pre-drilled hole is provided in the bone, into which it is desired that the screw 120 be disposed. The hole may be pretapped, or the external threading 128 of the screw 120 may include a self-tapping lead edge. In either event, the head 122 of the screw 120 is inserted downward, through the interior passage 158 of the coupling element 150, with the head 122 of the screw 120 nesting in the lower socket portion 152. At this point in the assembly process, the screw 120 and the coupling element 150 have the capacity to rotate relative to one another.

By orienting the coupling element 150 and the screw 120 coaxially, a screw-driving tool may be aligned with the recess 130 in the head 122 of the screw 120 so that it may be driven into the preformed hole in the bone.

Subsequent to the screw 120 being driven into the hole, the coupling element 150 may be rotated and agulated relative to the screw 120, to an angle such that support rod 190 may be properly nested within the rod receiving locus 166. As shown in FIG. 5, the bottom 191 of the rod 190 seats on the top of the head 122, and not fully on the bottom curved surface 174 of the channels 166.

After the rod 190 is appropriately positioned therein, the top locking nut 185 is threaded onto the threading 176 of the upwardly extending members 171,172. The lower surface 188 of the nut 185 seats against the top surface 192 of the rod 190. As the nut 185 rotates, and descends relative to the coupling element 150, the rod 190 is driven downward, causing the rod 190 and the head 122 of the screw 120 to translate downward slightly. This downward translation permits the bottom 191 of the rod 190 to seat against the bottom surface 174, and causes the head 122 of the screw 120 to be crush locked to the inwardly curved surface 156 of the coupling element 150.

In addition, the downward force of the bottom surface 188 of the nut 185 against the rod 190, as well as the upward counter-force provided by the bottom surface 174 of the channels 166 causes the rod 190 to be locked. This locking prevents the rod 190 from sliding relative to the assembled structure (along an axis which is perpendicular to the plane of FIG. 5). The full insertion of the top locking nut 185, therefore, locks the rod 190 to the coupling element 150, as well as the screw 120 to the coupling element 150.

Figure 6:
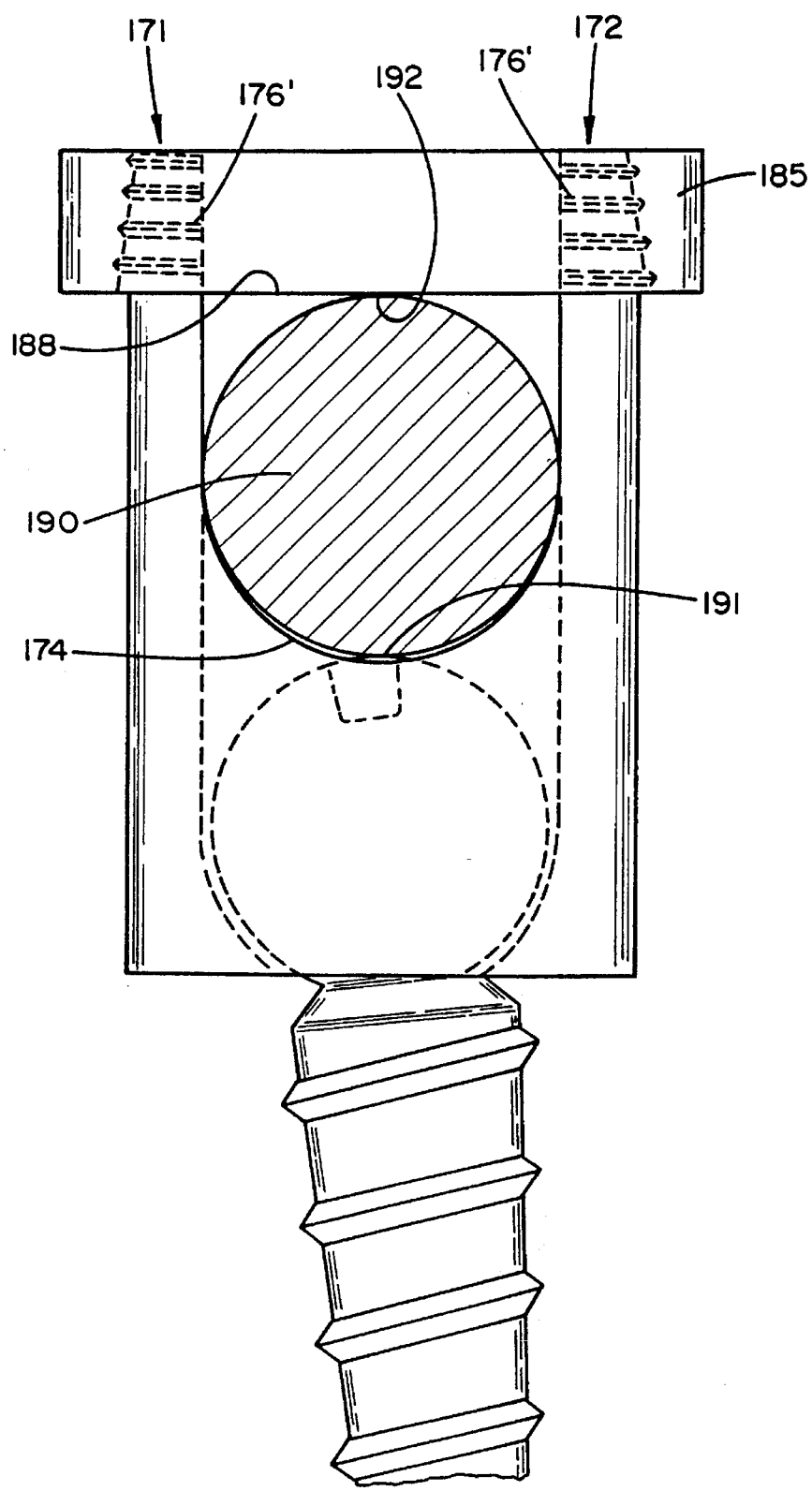
FIG. 6 is a side cross-sectional view of the present invention in its fully assembled disposition having a rod securely locked therein, wherein the top threading of the coupling element includes a taper.

Referring now to FIG. 6, a preferred variation of the above described embodiment is shown. In this preferred variation, the tops of the upwardly extending members 171,172, and more particularly the threading 176' thereon, includes an downwardly and outwardly biased taper. In this variation, therefore, the downward translation of the top locking nut 185 causes the upwardly extending members 171,172 to deflect inwardly, crush locking the rod 190 in the rod receiving channels 166 from the sides. This locking is in addition to the securing provided by the seating of the bottom 191 of the rod 190 against the curved bottom 174 of the channel 166, and the seating of the bottom 188 of the top locking nut 185 on the top 191 of the rod 190.

While there has been described and illustrated embodiments of a polyaxial screw and coupling element assembly for use with posterior spinal rod implantation apparatus, it will be apparent to those skilled in the art that variations and modifications are possible without deviating from the broad spirit and principle of the present invention. The present invention shall, therefore, be limited solely by the scope of the claims appended hereto.

We claim:

1. A orthopedic rod implantation apparatus having polyaxial screw and coupling elements, comprising:

at least one elongate rod;

at least one polyaxial screw having a curvate head;

at least one coupling element, including
an axially extending interior passage having an inwardly curvate surface at a lower end thereof, said inwardly curvate surface defining a socket wherein said semispherical head may be polyaxially mounted for selected angular adjustment of the screw relative to the coupling element,
a pair of opposing channels formed in the top of said coupling element, said channels defining a rod receiving locus,
a pair of upwardly extending members having an exterior threading disposed on uppermost portions thereof; and at least one top locking nut, mateable with said threading, for locking a rod in said rod receiving locus, and for locking said the semispherical head of said screw in the socket of said coupling element by direct contact between said rod and said semispherical head, thereby locking said screw at said selected angle.

2. The assembly as set forth in claim 1, wherein said uppermost portions of said pair of upwardly extending members comprises a taper, whereby the downward translation of the corresponding top locking nut thereon provides and inwardly deflecting force.

* * * * *